(12) United States Patent
Totman et al.

(10) Patent No.: US 10,912,709 B2
(45) Date of Patent: Feb. 9, 2021

(54) HAND MOUNTED CPR CHEST COMPRESSION MONITOR

(71) Applicant: ZOLL Medical Corporation, Chelmsford, MA (US)

(72) Inventors: Mark H Totman, Winchester, MA (US); Timothy S McGough, Merrimack, NH (US); David Barash, Boston, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 1115 days.

(21) Appl. No.: 15/267,202

(22) Filed: Sep. 16, 2016

(65) Prior Publication Data
US 2017/0042762 A1 Feb. 16, 2017

Related U.S. Application Data

(63) Continuation of application No. 13/294,689, filed on Nov. 11, 2011, now abandoned.
(Continued)

(51) Int. Cl.
*A61H 31/00* (2006.01)
*A61B 5/00* (2006.01)
(Continued)

(52) U.S. Cl.
CPC .......... *A61H 31/005* (2013.01); *A61B 5/1135* (2013.01); *A61B 5/681* (2013.01); *A61B 5/6831* (2013.01); *A61H 31/00* (2013.01); *A61H 31/004* (2013.01); *A61H 31/007* (2013.01); *G06F 1/1626* (2013.01); *G06F 1/1694* (2013.01); *G06F 3/014* (2013.01); *A61B 2505/01* (2013.01); *A61B 2560/0431* (2013.01); *A61H 2201/501* (2013.01);
(Continued)

(58) Field of Classification Search
CPC .......... A61H 7/00; A61H 7/001; A61H 23/06; A61H 31/00; A61H 31/004; A61H 31/005; A61H 31/007; A61H 2031/001; A61H 2031/002; A61H 2031/003; A61H 2201/1635; A61H 2201/1638; A61H 2201/5058; A61H 2201/5084; A61H 2201/5097; A61H 2201/501; A61H 2201/5007; A61B 5/681; A61B 2505/01
See application file for complete search history.

(56) References Cited

U.S. PATENT DOCUMENTS

| 5,534,851 A | 7/1996 | Russek |
| 5,960,085 A * | 9/1999 | de la Huerga ........ A61J 1/1437 340/5.61 |
| 6,390,996 B1 | 5/2002 | Halperin |
| 7,122,014 B2 | 10/2006 | Palazzolo et al. |

(Continued)

*Primary Examiner* — Colin W Stuart
(74) *Attorney, Agent, or Firm* — ZOLL Medical Corporation

(57) ABSTRACT

A chest compression monitor for measuring the depth of chest compressions achieved during CPR. A displacement detector produces a displacement signal indicative of the displacement of the CPR recipient's chest toward the recipient's spine. A signaling mechanism provides chest compression indication signals prompting a CPR provider to provide a chest compression force at a desired depth and rate. The device is held to the dorsal surface of the hand during use and provides a display for feedback, which is readily visible to the CPR provider.

20 Claims, 3 Drawing Sheets

Related U.S. Application Data

(60) Provisional application No. 61/413,278, filed on Nov. 12, 2010.

(51) Int. Cl.
    *A61B 5/113*     (2006.01)
    *G06F 3/01*     (2006.01)
    *G06F 1/16*     (2006.01)

(52) U.S. Cl.
    CPC ................ *A61H 2201/5007* (2013.01); *A61H 2201/5015* (2013.01); *A61H 2201/5041* (2013.01); *A61H 2201/5084* (2013.01); *G06F 2200/1633* (2013.01); *G06F 2200/1637* (2013.01)

(56) References Cited

U.S. PATENT DOCUMENTS

| | | |
|---|---|---|
| 7,220,235 B2 | 5/2007 | Geheb et al. |
| 8,034,006 B2 | 10/2011 | Celik-Butler et al. |
| 8,147,433 B2 | 4/2012 | Halperin et al. |
| 8,428,664 B1 | 4/2013 | Wyers |
| 2006/0270952 A1* | 11/2006 | Freeman ............... A61H 31/005 601/41 |
| 2008/0171311 A1 | 7/2008 | Centen et al. |
| 2008/0300518 A1* | 12/2008 | Bowes ................. A61H 31/007 601/41 |
| 2010/0022904 A1 | 1/2010 | Centen |
| 2011/0009164 A1 | 1/2011 | Amiri |
| 2011/0028885 A1* | 2/2011 | Eggers ................ A61M 5/1413 604/19 |
| 2011/0117878 A1 | 5/2011 | Barash et al. |

\* cited by examiner

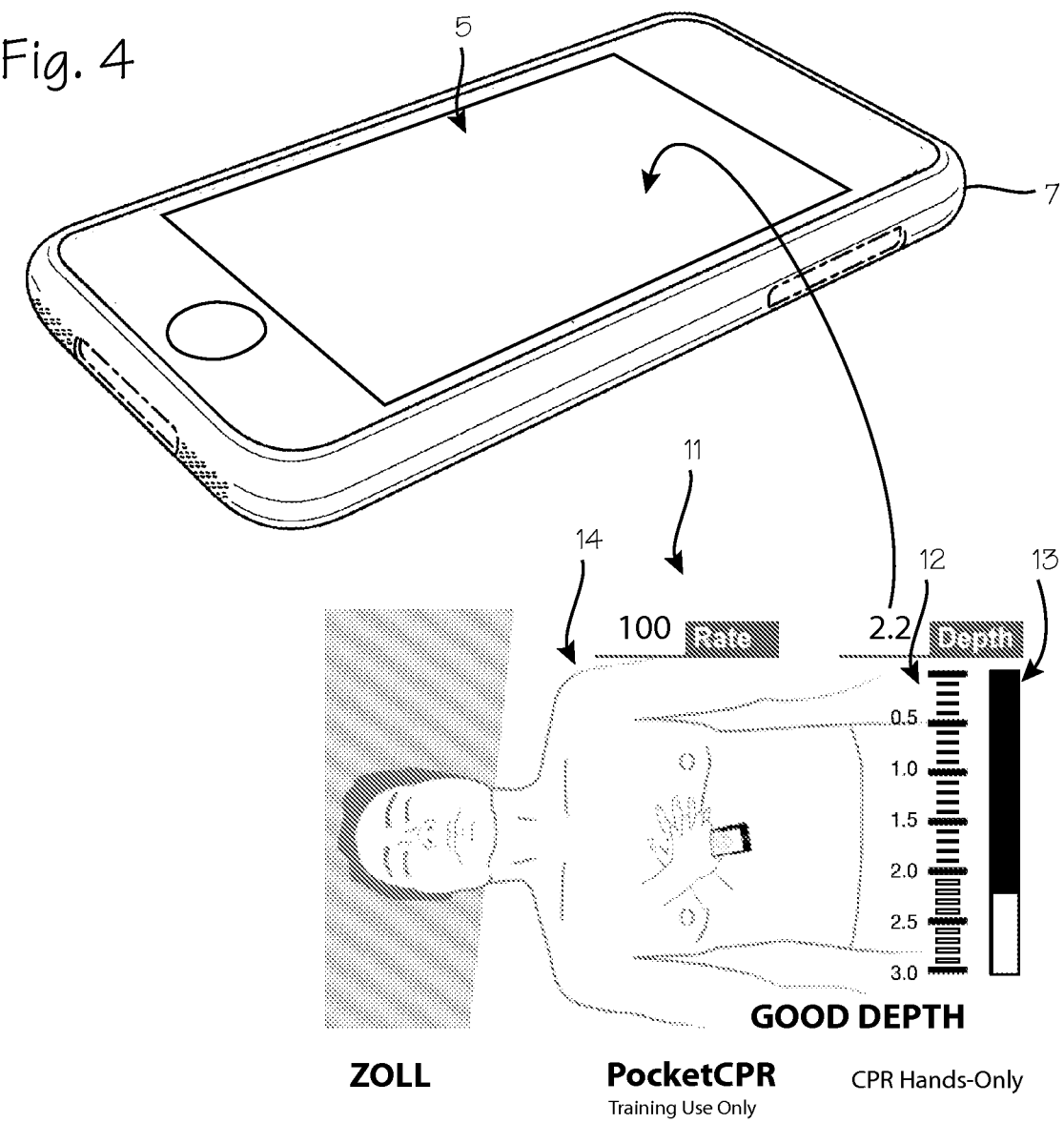

HAND MOUNTED CPR CHEST COMPRESSION MONITOR

CROSS-REFERENCE TO RELATED APPLICATIONS

This application is a continuation under 35 U.S.C. § 120 of U.S. patent application Ser. No. 13/294,689 filed Nov. 11, 2011, which claims benefit under 35 U.S.C. § 119(e) to U.S. Provisional Application Ser. No. 61/413,278 filed Nov. 12, 2010. All subject matter set forth in each of the above referenced applications is hereby incorporated by reference in their entirety into the present application as if fully set forth herein.

TECHNICAL FIELD

The present invention relates to a device for aiding in the administration of cardiopulmonary resuscitation (CPR).

BACKGROUND

Chest monitoring during the course of CPR is now possible with the Real CPR Help® technology marketed by ZOLL Medical Corporation. This technology is described in U.S. Pat. Nos. 6,390,996, 7,108,665, and 7,429,250, and includes the use of an accelerometer to measure accelerations of the chest and calculating the depth of each compression from the acceleration signal. The technology is used in ZOLL's Real CPR Help®. compression depth monitoring system to provides real-time rate and depth CPR feedback for manual CPR providers. Commercially, it is implemented in ZOLL's electrode pads, such as the CPR-D•Padz® electrode pads. It is also implemented for training use in the PocketCPR® iPhone app.

U.S. Pat. No. 6,390,996 to Halperin, as well as U.S. Pat. No. 7,122,014 to Palazzolo, described chest compression monitors capable of determining chest compression depth accurately during repeated rapid chest compressions required by CPR. In some embodiments, the devices of Halperin and Palazzolo were adapted to be fixed to CPR providers wrist during CPR, and in other embodiments the chest compression monitor was adapted to be placed between the CPR provider's hand and the patient's sternum during CPR. In both cases, the CPR chest compression monitor is held in fixed relationship to the chest during use, and the chest compression module is operable to determine the depth of each chest compression based on acceleration data from accelerometers in the chest compression module, without input from other sources, especially without input of data from other sensors fixed in space or remote from the compression module. U.S. Pat. Nos. 6,390,996 and 7,122,014 are hereby incorporated in their entirety.

U.S. Pub. 2008/0171311 to Centen discloses a CPR chest compression depth monitor essentially identical to that disclosed in Halperin. In one of his embodiments, Centen places a display on the dorsal surface of the bottom hand of the rescuer while placing the accelerometers on the ventral or palmar side of the bottom hand of the rescuer. The components of the chest compression module are dispersed about a glove which is worn by the CPR provider while providing CPR compressions.

SUMMARY

The devices and methods described below aid in the proper application of CPR in various situations in order to substantially improve the survival rate of CPR recipients with a CPR compression monitor adapted to be secured to the CPR providers hand, with a housing, including accelerometers, a processor, and output means such as a display and speaker secured on the dorsal side of the rescuers hand. Manual CPR requires using both hands, one on top of the other, with the heel of the bottom hand in contact with the patient's sternum, to repeatedly compress the chest. The chest compression module described below is adapted to fit over the hand, disposed on the dorsal side of the upper hand (the back of the hand) rather than the palmar side of the upper hand or lower hand, of a CPR provider. The system provides for measuring and prompting chest compressions to facilitate the effective administration of CPR.

As described in U.S. Pat. No. 6,390,996 to Halperin, a hand-held CPR chest compression monitor accurately measures the rate and depth of chest compressions during the administration of CPR. The device provides prompts the rescuer to encourage correct compressions. It requires a minimum amount of set-up time, is intuitive in its operation, and is easy to use. The device is preferably small, light, and inexpensive to manufacture and distribute. Current smart phones, multifunction watches which are already fitted with accelerometers, such as the Apple iPhone®. and the Texas Instruments eZ430-Chronos® wireless watch, make suitable platforms for the necessary software. In particular, watches such as the eZ430-Chronos® wireless watch provide the desired accelerometer, processor, display, enunciator, housing, and strap for securing the housing to the back of the hand.

The system measures and provides prompts for chest compressions to facilitate the effective administration of CPR by a rescuer. The system comprises a displacement detector for producing an output signal indicative of a displacement of a CPR recipient's chest toward the CPR recipient's spine. A signaling mechanism provides signals corresponding to chest compression forces to be applied to the chest, frequency of compressions to be provided to help the CPR provider provide compressions within desired frequency range and maintain the chest displacement within a desired distance range.

The displacement detector comprises a motion detector for determining an amount of CPR induced motion of the chest in relation to the spine. A converter converts an output signal produced by the motion detector into a distance value. The signaling mechanism comprises a mechanism for comparing the distance value to a desired range of distance values, and for signaling directions regarding chest compression force and frequency in accordance with whether the value falls within the desired range of distance values.

DESCRIPTION OF DRAWINGS

FIG. 4 illustrates the display provided by the chest compression monitor.

DETAILED DESCRIPTION

Figure 1:
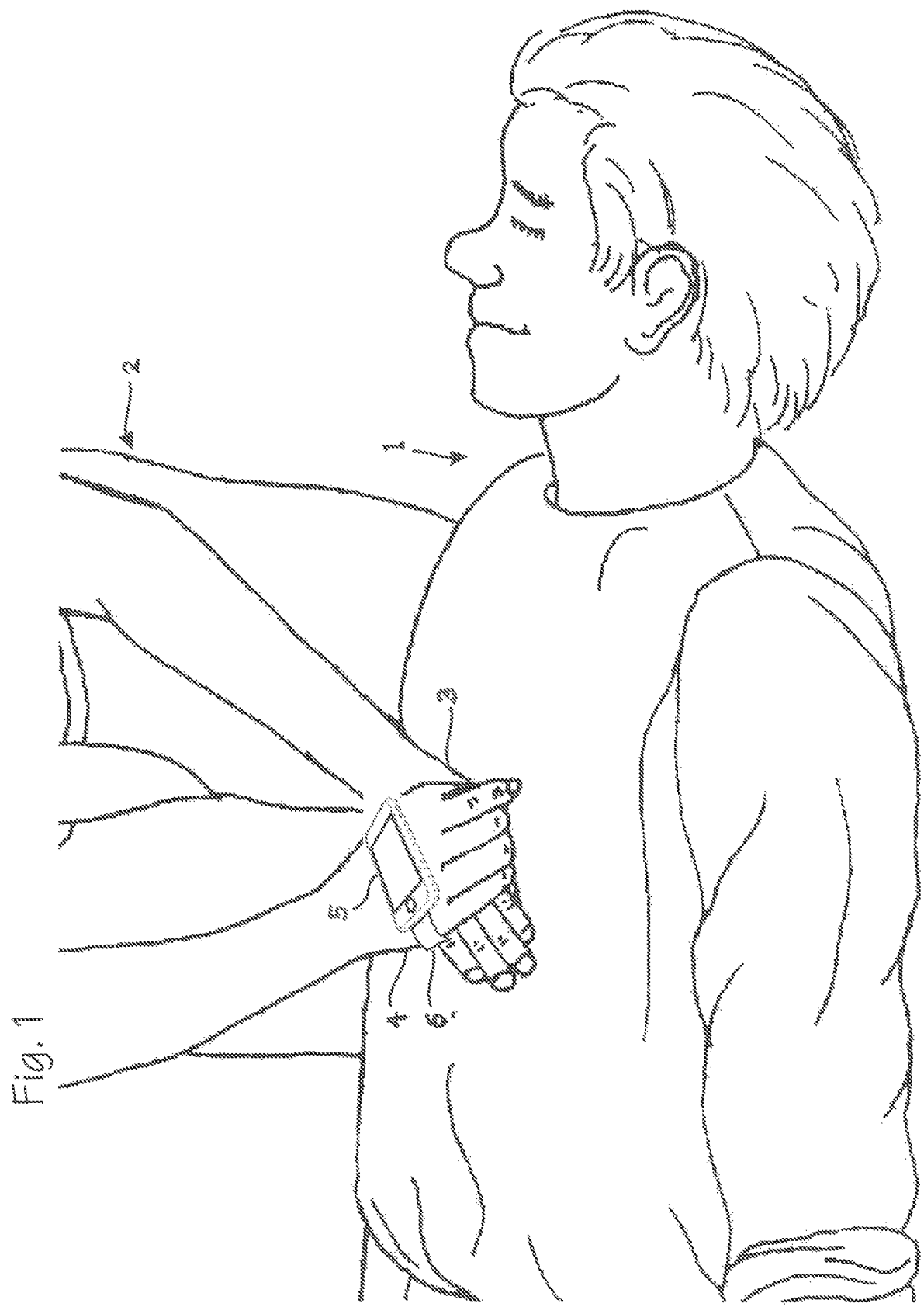
FIG. 1 shows a rescuer administering CPR to a CPR recipient utilizing a CPR monitoring device.

FIG. 1 illustrates a chest compression monitor in use. In FIG. 1, a cardiac arrest patient 1 is shown supine, in a suitable position for the application of CPR, with a CPR provider 2 kneeling over the chest of the patient. Per the American Heart Association Emergency Cardiac Care guidelines for providing CPR (and the European Resuscitation Council/International Liaison Committee on Resuscitation guidelines), the CPR provider has placed one hand 3 over the patient's sternum (with the heel of the hand impinging on the sternum) and has placed the other hand 4 over the first hand. Also, the CPR provider has secured a CPR chest compression monitor 5 to the back of his second hand (the dorsal surface of the hand) with the strap or band 6 wrapped around the hand. After initiating operation of software on a processor disposed within the housing of the chest compression monitor, the CPR provider provides a number of chest compressions. As detailed in the Halperin patents, an accelerometer within the housing measures the acceleration of the chest compression monitor (and, thus, the acceleration of the CPR provider's hands and the patient's chest, specifically the sternum and the anterior surface of the chest), and provides acceleration data to a processor within the housing. The processor receives acceleration data from the accelerometer within the housing, computes the depth of compressions and the rate of compressions, and provides output to the CPR provider regarding the depth of compressions, the rate of compressions, the timing of ventilation pauses or other CPR compression parameters. This output can be visual, provided on a display, and audible, provided through speakers on the chest compression monitor. Visual output may be in the form of a bar icon which depicts the depth of compression, or in the form of a depiction of a chest wall moving up and down combined with a graphical representation of the desired depth and the measured depth. Audible feedback may be in the form of prompts to perform compressions more deeply, or less deeply, or more or less rapidly.

The system accurately determines compression depth without reference to any data derived from fixed sources, and floats freely with the CPR provider's hands. The microprocessor is programmed to determining the start of a compression without reference to a signal derived from a source external to the module, and thereafter calculate downward displacement of the chest using the acceleration signal; said microprocessor further programmed to output a compression signal. The microprocessor is also programmed to determine the start and end of each compression based on the acceleration signal, a zero-point of acceleration and changes in the direction of velocity of the module.

Figure 2:
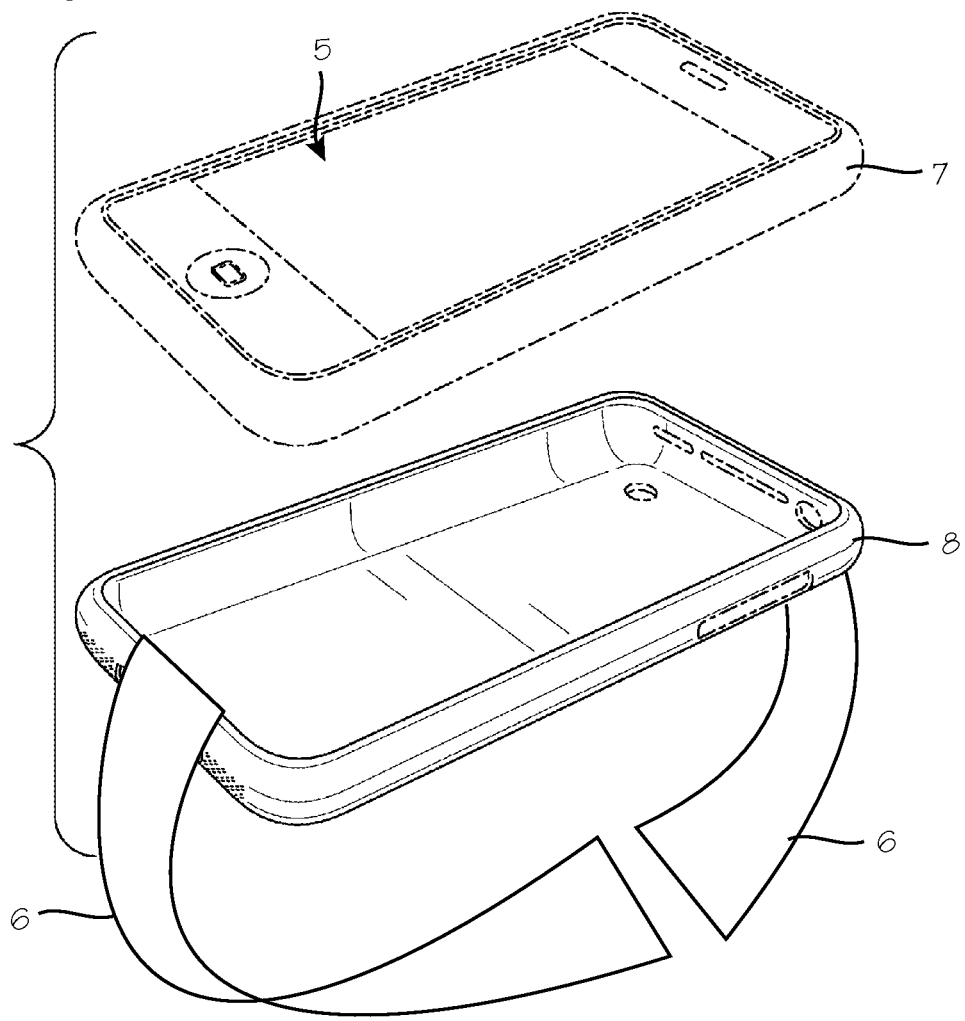
FIG. 2 shows a hand-held CPR chest compression monitor with a holder and strap adapted to secure the chest compression monitor over the CPR provider's hand.
Figure 3:
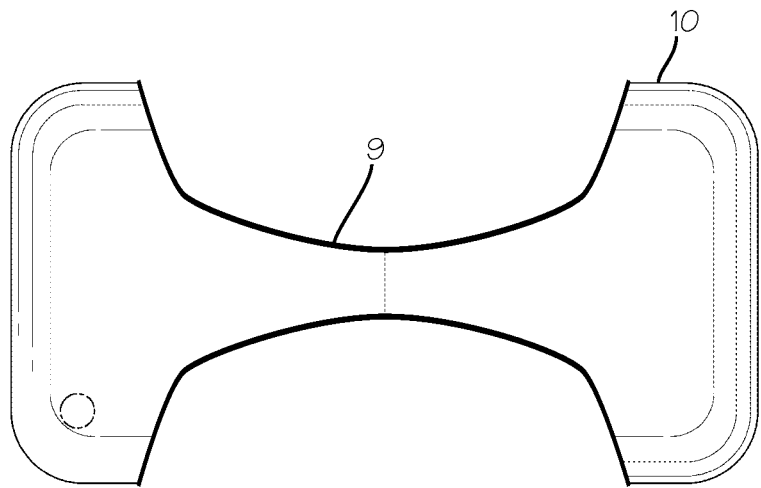
FIG. 3 illustrates cover for the hand-held CPR chest compression monitor.

FIG. 2 illustrates a hand-mounted CPR chest compression monitor 5 for measuring the rate and depth of chest compressions during the administration of CPR. The monitor is a specific implementation of a monitoring system for measuring and prompting chest compressions to facilitate the effective administration of cardiopulmonary resuscitation (CPR). The system is based in a housing 7, which may be the housing of a smart phone or wristwatch, or similar housing, combined with a strap suitable for holding the housing to the back of the hand. Any suitable housing may be used, and any suitable releasable fixing mechanism may be used in place of the strap, so long as it is releasable in the sense that may be quickly and easily used to secure the chest compression monitor to the hand. In this case, the housing is an iPhone®, held within a silicone cover which functions as a holder, which in turn is connected a silicone strap which is sized to fit around the hand of the user without excessive slack. The strap may be incorporated into the back of the silicone cover 8. If sufficiently elastic, the back of the cover can be trimmed away to leave a strap like web 9 connecting between the top and bottom of the housing, and this strap like web can be used as the necessary strap. This is shown in FIG. 3, which shows a cover 10 comprising receiving pouches for each end of the smart phone, connected by a web. The web is sufficiently elastic so that it conforms to the back of the phone when relaxed, but can easily stretch to allow the CPR provider's hand to fit between the smart phone and the web.

For use with a watch-like chest compression monitor, the strap may be an easily expandable silicone band. The strap in this case should be elastic enough such that, when fully relaxed it fits closely to the wrist of the CPR provider, yet may be stretched to encompass the hand securely yet comfortably. The strap may also be adjustable between a first size that maintains the housing on the wrist without excess slack and a second larger size that maintains the housing on the back of the hand without excess slack.

The housing, whether a pre-existing smart phone, programmable watch, or dedicated chest compression monitor, houses the microprocessor, accelerometer, display, speaker or enunciator, and necessary input mechanisms (where discrete input mechanisms are used, rather than a touch screen with touch-operable input icons). The accelerometer produces an acceleration signal corresponding to the acceleration of the chest compression monitor, which is output to the microprocessor which produces and outputs a displacement signal indicative of the displacement of a CPR recipient's chest toward the recipient's spine. The microprocessor is also programmed to operate the speaker or enunciator to provide audible signals communicating the sufficiency or insufficiency of compressions, or prompting the CPR provider with audible pacing signals to help the CPR provider maintain the desired rate of compressions.

FIG. 4 illustrates the display provided by the chest compression device 5. The display 11 is provided through an LCD display, such as the large display of the smart phone depicted in FIG. 3. The display shows a scale 12 depicting the desired 2 inches of compression, and a second column 13 that provides an active depth indication bar which fills in green, along the scale, to depict the actual depth of the immediately preceding compression, or an average of the last few compressions. In the illustration, the depth indication bar has been created by the microprocessor, and displayed on the display, to indicate that the compression is in the acceptable range, at about 2.2 inches (which reported on the display below the scale). When compression depth is in the acceptable range, the depth indication bar is filled in green, and when the compression depth is outside the desired range, the depth compression bar is filled in red. On the top portion of the display, the display is operated by the microprocessor to show the text message describing the recent compression, indicating that it was adequate. The microprocessor can also present text to prompt the user to provide deeper compression, warn the user to provide shallower compression, to provide more rapid compressions, etc. Also in the center of the display is an area 14 used to depict the suggested mode of use of the device. In the illustrated display, the microprocessor is presenting a suggestion for proper use of the chest compression monitor alone, without a strap, which is an acceptable option when the cover and strap of FIG. 2 are not available. As shown in the illustration, the chest compression monitor is held between the upper and lower hand so that the display extends from under the upper hand and is visible to the CPR provider. The display also includes a depiction of the patient and a depiction of proper placement of the CPR provider's hands. The CPR provider's hands are depicted in a hands screen element which is modified by the processor, to enlarge and shrink repeatedly to prompt the user to start compression, and to indicate that compressions should continue. If the CPR provider has provided input to the device to indicate that he will provide CPR with rescue breathing, the microprocessor will periodically stop the pulsating enlargement of the hands screen element and prompt the CPR provider to provide rescue breathing, and will reinitiate pulsating enlargement of the hands screen element to indicate when the compressions should be restarted after a ventilation pause.

Additional features may be incorporated into the system. Memory may be provided so that the processor can store historical compression data. Removable flash memory may be used, from which compression data can be retrieved by any computer, and communications hardware (USB, Bluetooth®, etc.) may be provided so that compression data may be retrieved directly from the device. Chest compression data can then be retrieved by a general purpose computer and analyzed as desired to determine the effectiveness of compressions and comparing the historical compression data with other parameters measured during CPR. Communications hardware and associated software may be used to transmit chest compression data (or other CPR related data) to a bedside monitor or a remote monitor, which may in turn be programmed to notify additional potential responders that CPR is in progress. The device or the remote monitor can also be programmed to coordinate communications with the typical hospital rapid response team. Provided that a device is in the possession of a number of RRT members, one device or a central control system can be programmed to communicate with devices held by members of the RRT, and those members can use communications capabilities of the device to learn of cardiac arrest within the hospital, and respond with text, preprogrammed responses, or audio, indicating their ability to respond and provide aspects of cardiac arrest therapy. If most or all hospital employees possess a device, other important employee notifications and hospital specific codes can be provided through the system, and desired response to various codes can be transmitted from the device to the central control system, thereby quickly confirming that necessary responses to various codes have occurred.

The housing may be combined also with personnel identification card used by hospital employees, and, where the benefits of prefabricated housing/accelerometer/microprocessor are not desired, the components may be incorporated into a badge-like or card-like device that takes the place of ID tags currently used. The device may be used to track the location of hospital staff, which is particularly important to ensure, for example, that ICU's are adequately staffed. The device may be combined with authentication protocols and security information, and may be used in combination with security systems that control access to spaces within the hospital, security systems that control access to ambulances and emergency vehicles, and security systems that control access to emergency medical equipment such as defibrillators, as described in U.S. Pat. No. 7,666,154 to Bystrom. In hospital, the device may be used in conjunction with proximity sensors or ID sensors to track employee working hours.

The memory and microprocessor within the device can also be used to store and display instructions for common hospital procedures, including various codes. ACLS guidelines, hospital-specific cardiac arrest procedures, instructions for responding to Code Red, Code Pink, and other codes can be provided for convenient review by users.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

What is claimed is:

1. A first compression monitor configured to be associated with a plurality of compression monitors, the first compression monitor being adapted to be associated with a member of a rapid response team (RRT) in a hospital environment, wherein the first compression monitor and each of the plurality of compression monitors are configured to be carried by a different RRT member, the first compression monitor comprising:
   a device configured to:
      generate signals indicative of chest compressions,
      determine chest compression data based on the signals indicative of the chest compressions,
      store the chest compression data, and
      transmit compression information from the first compression monitor to be received by a different compression monitor of the plurality of compression monitors as a notification that CPR is in progress, wherein the compression information is based on the chest compression data;
   a housing configured as a holder for the device; and
   a strap connected to the housing and adapted to secure the housing to a hand of the member of the RRT.

2. The first compression monitor of claim 1 wherein the first compression monitor is configured to coordinate communications amongst the plurality of compression monitors adapted to be associated with the RRT.

3. The first compression monitor of claim 1 wherein the device is configured to store the chest compression data comprising historical chest compression parameters.

4. The first compression monitor of claim 3 wherein the determined chest compression data comprises current chest compression parameters and further wherein the device is configured to compare the historical chest compression parameters with current chest compression parameters and determine CPR effectiveness information.

5. The first compression monitor of claim 3 wherein the device is configured to transmit the historical chest compression parameters to a central control system adapted to be associated with the plurality of compression monitors.

6. The first compression monitor of claim 1 wherein the device is configured to receive texts, preprogrammed responses, and audio responses from the plurality of compression monitors.

7. The first compression monitor of claim 1 wherein the device is configured to send, from the first compression monitor to the different compression monitor, at least one of hospital information, RRT member identification information, RRT member location information, CPR guideline information, and patient information.

8. The first compression monitor of claim 7 wherein the hospital information includes a hospital code and a response to the hospital code.

9. The first compression monitor of claim 1 wherein the device further stores historical chest compression parameters.

10. The first compression monitor of claim 1 wherein the device supports at least one of universal serial bus (USB) communication and wireless communication.

11. The first compression monitor of claim 1 further wherein the housing comprises a strap configured to secure the first compression monitor to the dorsal surface of the hand of the member of the RRT at least while the member of the RRT is manually compressing the chest of a patient.

12. The first compression monitor of claim 1 wherein the device comprises one or more accelerometers.

13. The first compression monitor of claim 12 wherein the chest compression data comprises an acceleration of the chest of a patient, a depth of chest compression, an average depth of chest compression, a rate of chest compression, a timing of ventilation pauses, a start and end of each compression, a zero-point of acceleration, a velocity, and a change in a direction of the velocity.

14. The first compression monitor of claim 1 wherein the device is configured to communicate according to authentication protocols.

15. The first compression monitor of claim 1 wherein the device is compatible with one or more of proximity sensors and identification sensors in the hospital environment.

16. The first compression monitor of claim 1, wherein the first compression monitor is remote from the different compression monitor of the plurality of compression monitors.

17. The first compression monitor of claim 1, wherein the first compression monitor and each of the plurality of chest compression monitors are each configured to transmit and receive notifications that CPR is in progress.

18. The first compression monitor of claim 1, wherein the first compression monitor is adapted to communicate with compression monitors of the plurality of compression monitors.

19. The first compression monitor of claim 1, wherein the strap comprises an elastic band configured to be wrapped around the hand of the member of the RRT.

20. A hospital system for use by a rapid response team (RRT) in a hospital environment, the hospital system comprising:
  a plurality of devices wherein at least one of the plurality of devices is configured to coordinate communications amongst the plurality of devices, the plurality of devices including at least one compression monitor,
  and further wherein the at least one compression monitor comprises:
  a device configured to:
    generate signals indicative of chest compressions,
    determine chest compression data based on the signals indicative of chest compressions,
    store the chest compression data, and
    transmit compression information from the at least one compression monitor to one or more other of the plurality of devices as a notification that CPR is in progress, wherein the compression information comprises the chest compression data;
  a housing configured as a holder for the device; and
  a strap connected to the housing and adapted to secure the housing to a hand of a member of the RRT.

* * * * *